United States Patent
Xie et al.

(10) Patent No.: US 12,055,387 B2
(45) Date of Patent: Aug. 6, 2024

(54) **METHOD FOR DETECTING TEXTURE OF *TAKIFUGU OBSCURUS***

(71) Applicant: Shanghai Ocean University, Shanghai (CN)

(72) Inventors: Jing Xie, Shanghai (CN); Peiyun Li, Shanghai (CN); Jinfeng Wang, Shanghai (CN); Yueming Chen, Shanghai (CN)

(73) Assignee: Shanghai Ocean University, Shanghai (CN)

( * ) Notice: Subject to any disclaimer, the term of this patent is extended or adjusted under 35 U.S.C. 154(b) by 287 days.

(21) Appl. No.: 17/691,013

(22) Filed: Mar. 9, 2022

(65) Prior Publication Data

US 2022/0196400 A1 Jun. 23, 2022

(30) Foreign Application Priority Data

Jan. 17, 2022 (CN) .......................... 202210048169.9

(51) Int. Cl.
| | |
|---|---|
| G01B 21/30 | (2006.01) |
| A01N 1/00 | (2006.01) |
| G01N 1/04 | (2006.01) |
| G01N 1/42 | (2006.01) |
| G01N 33/12 | (2006.01) |

(52) U.S. Cl.
CPC ............... *G01B 21/30* (2013.01); *A01N 1/00* (2013.01); *G01N 1/04* (2013.01); *G01N 1/42* (2013.01); *G01N 33/12* (2013.01)

(58) Field of Classification Search
CPC .......... G01B 21/30; G01N 33/12; G01N 1/04; G01N 1/42; A01N 1/00
See application file for complete search history.

(56) References Cited

U.S. PATENT DOCUMENTS

| 4,908,703 A | * | 3/1990 | Jensen | G01N 33/12 |
| | | | | 348/89 |
| 6,770,318 B1 | * | 8/2004 | Roussell | A23L 17/70 |
| | | | | 426/643 |
| 2008/0199575 A1 | * | 8/2008 | Morkemo | A23L 17/00 |
| | | | | 426/303 |
| 2018/0036773 A1 | * | 2/2018 | Arnason | A22C 25/08 |
| 2019/0353587 A1 | * | 11/2019 | O'Brien | G01J 3/2803 |

FOREIGN PATENT DOCUMENTS

| CN | 103675220 | * | 3/2014 |
| CN | 106720922 | * | 5/2017 |
| CN | 110210680 A | | 9/2019 |
| CN | 111724350 A | | 9/2020 |
| JP | 2004-267149 | * | 9/2004 |
| JP | 2015-040852 | * | 3/2015 |

* cited by examiner

*Primary Examiner* — Helen C Kwok

(57) ABSTRACT

A method for detecting a texture of *Takifugu obscurus*, including: (S1) removing internal organs and skin of the *Takifugu obscurus* followed by washing and drying; and removing a head and cutting a flesh on two sides of the *Takifugu obscurus* along a spine; (S2) cutting a plurality of cylindrical samples with the same shape and size along both sides of the flesh followed by transfer to a pre-cooled petri dish; allowing a cross section of the samples to cling to the petri dish followed by fixing with a petri dish cover; and storing the petri dish in seal at 0-4° C.; (S3) detecting, by a texture analyzer, a texture of each cylindrical sample; and averaging detection results of the samples as a result of the texture of the *Takifugu obscurus*.

8 Claims, 1 Drawing Sheet

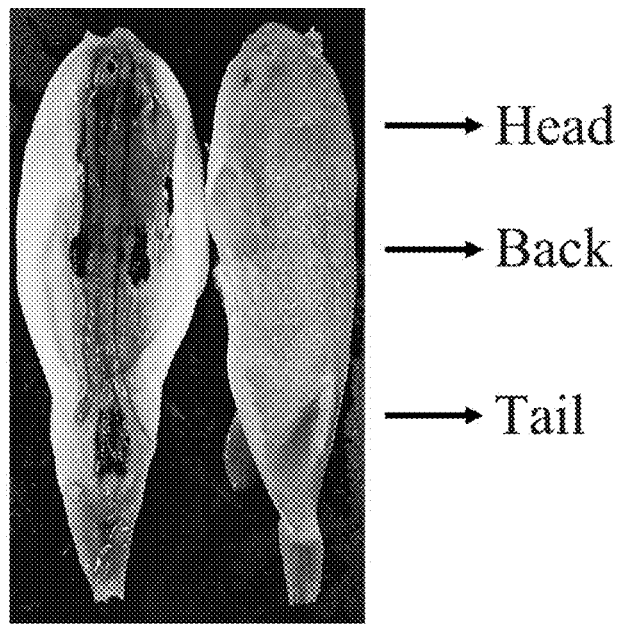

METHOD FOR DETECTING TEXTURE OF TAKIFUGU OBSCURUS

CROSS-REFERENCE TO RELATED APPLICATIONS

This application claims the benefit of priority from Chinese Patent Application No. 202210048169.9, filed on Jan. 17, 2022. The content of the aforementioned application, including any intervening amendments thereto, is incorporated herein by reference in its entirety.

TECHNICAL FIELD

This application relates to texture analysis of fish, and more specifically to a method for detecting a texture of Takifugu obscurus.

BACKGROUND

Takifugu obscurus is a traditional economically-valuable fish in the coastal areas of China, which is widely distributed in the East China Sea, the Yellow Sea, the Bohai Sea and the Yangtze River basin, and is honored as one of the "three delicious fish species in the Yangtze River". In addition to the delicious taste, the Takifugu obscurus is also rich in nutrients. Particularly, the Takifugu obscurus contains 8 essential amino acids and 10 non-essential amino acids, and a ratio of the essential amino acids to the non-essential amino acids is as high as 68.34%, which is superior to an ideal standard recommended by Food and Agriculture Organization of the United Nations/World Health Organization (FAO/WHO). Moreover, the Takifugu obscurus is considered as a high-quality protein and mineral element (including potassium, calcium and zinc) source, while the fat content is relatively low, and thus is widely appreciated. However, the fresh Takifugu obscurus is prone to deterioration under the action of an exogenous microorganism and an endogenous enzyme, resulting in economic loss and environmental pollution. Therefore, extensive researches have been carried out on the preservation of Takifugu obscurus. The detection of related indexes is essential to characterize the preservation effect. During the storage, due to the activities of endogenous enzymes, hydrolysis of muscle proteins and destruction of connective tissues, the muscle of Takifugu obscurus softens gradually accompanied by a gradual decline in the springiness and resilience, indicating a significantly change in the texture. As a result, the texture is considered as an important indicator to evaluate the quality of Takifugu obscurus. Traditionally, the texture analysis of Takifugu obscurus is carried out at room temperature, and there is no unified standard (collection part, shape and size of muscle), resulting in a large error in the detection results.

SUMMARY

An object of the present disclosure is to provide a method for detecting a texture of Takifugu obscurus, which can provide a convenient sampling method and detection parameters for the texture analysis of Takifugu obscurus.

The technical solutions of the present disclosure are described as follows.

A method for detecting a texture of Takifugu obscurus, comprising:

(S1) removing internal organs and skin of the Takifugu obscurus followed by washing and drying; and removing a head of the Takifugu obscurus and cutting a flesh on two sides of the Takifugu obscurus along a spine of the Takifugu obscurus;

(S2) cutting a plurality of cylindrical samples with the same shape and size along two sides of the flesh followed by transfer to a pre-cooled petri dish;

allowing a cross section of each of the plurality of cylindrical samples to cling to the pre-cooled petri dish followed by fixing with a petri dish cover; and storing the petri dish in seal at 0-4° C.; and (S3) detecting, by a texture analyzer, a texture of each of the plurality of cylindrical samples; wherein detection parameters of the texture analyzer are set as follows: distance: 20-30 mm, post-test speed: 3-8 mm/s, and force: 8-12 g; and averaging detection results of the plurality of cylindrical samples as a detection result of the texture of Takifugu obscurus.

In an embodiment, an upper end of flesh is cylindrical and has a diameter of 2.0-2.5 cm; a lower end of the flesh is flat and has a width of 2.3-2.8 cm; and a length of the flesh is 13-15 cm.

In an embodiment, the plurality of cylindrical samples are cut from a part of the flesh at a distance of 2.0 cm from a cross section of the upper end of the flesh.

In an embodiment, each of the plurality of cylindrical samples has a height of 1.5-2.0 cm and a diameter of 1.8-2.5 cm.

In an embodiment, the number of the plurality of cylindrical samples is greater than or equal to 2.

In an embodiment, the number of the plurality of cylindrical samples is 4.

In an embodiment, the petri dish is pre-cooled to 0-4° C.

In an embodiment, in step (S2), the petri dish containing the plurality of cylindrical samples is stored at 0-4° C. in a refrigeration device.

In an embodiment, after removed from the refrigeration device, the plurality of cylindrical samples are required to be transferred to the texture analyzer within 30 s.

Compared to the prior art, the present disclosure has the following beneficial effects.

Regarding the method of the present disclosure, the whole process is performed at a low temperature, which prevents the temperature fluctuation from affecting the sample quality to the greatest extent, and improves the detection accuracy of the texture. At the same time, multiple samples with the same shape and size are collected from the same part for detection, which reduces errors caused by difference in the sampling location, shape and size.

BRIEF DESCRIPTION OF THE DRAWINGS

This FIGURE schematically illustrates sampling locations of Takifugu obscurus according to Examples 1-3 of the present disclosure.

DETAILED DESCRIPTION OF EMBODIMENTS

Unless otherwise specified, the experiments in the following examples are conducted under conventional conditions or as instructed by the manufacturer, and the reagents or instruments are commercially available.

The technical solutions of the present disclosure will be described completely, accurately and clearly below with reference to the embodiments. Obviously, provided below are merely some embodiments of the disclosure, which are not intended to limit the disclosure. It should be understood that all other embodiments obtained by those skilled in the art based on the content disclosed herein without paying any creative effort shall fall within the scope of the present disclosure.

*Takifugu obscurus* samples used in Examples 1-3 were purchased from the same batch of products at the same location.

EXAMPLE 1

Provided herein was a method for detecting a texture of *Takifugu obscurus*, in which a sample was cut from a back of *Takifugu obscurus* (as shown in the FIGURE). The method was specifically performed as follows.

1. Pre-treatment of *Takifugu obscurus* and Preparation of Containers

1) The abdomen of *Takifugu obscurus* was quickly cut open using a sharp scissor for bloodletting. The gill was cut and removed with internal organs using fingers, and then the remaining internal organ was trimmed with the scissor. The skin of *Takifugu obscurus* was peeled off along a cut line on an upper abdomen. Eyes of *Takifugu obscurus* were removed using the scissor. The blood remaining in a spine of *Takifugu obscurus* was squeezed out, and then the *Takifugu obscurus* was cleaned with ice water.

2) A clean disposable plastic wrap was laid on a test bench, and the *Takifugu obscurus* was placed on the plastic wrap and dried naturally for 40 min.

3) Crushed ice was loaded to a foam box to ½ by volume of the foam box, where the foam box had a size of 30 cm×20 cm×20 cm.

4) A disposable petri dish with a diameter of 9 cm was prepared, and cooled in a 4° C. refrigerator for 2 h to load the *Takifugu obscurus* sample.

2. Cutting of *Takifugu obscurus* Samples for Texture Analysis

1) A special sampling knife was cleaned, disinfected with 75% alcohol and dried.

2) The head of *Takifugu obscurus* was crosswise cut off along a junction between the head and the upper abdomen with the special sampling knife, and a flesh on each side of *Takifugu obscurus* was cut off completely along the spine. An upper end of the flesh was cylindrical and had a diameter of about 2.2 cm; a lower end of the flesh was flat and had a width of 2.5 cm; and the flesh had a length of about 14 cm.

3) A cylindrical sample with a height of about 2.0 cm and a diameter of about 2.2 cm was cut in parallel at a distance of 2.0 cm from a cross section of the cylindrical end, and quickly placed in a pre-cooled petri dish in a refrigeration box at 0-4° C. The cross section of the cylindrical sample clung to the petri dish. A petri dish cover was covered to fix the cylindrical sample, and then the refrigeration box was closed.

4) Another cylindrical sample was cut from the same *Takifugu obscurus* sample again in the same way, and was put into the pre-cooled petri dish in the foam box. Then two sections of cylindrical samples were cut from another flesh through the same operation method, and were quickly put into the pre-cooled petri dish in the foam box. As a consequence, a total of four cylindrical samples with nearly the same shape, diameter and height were collected and placed together in the pre-cooled petri dish.

3. Texture Analysis

1) The texture analyzer and program were started, and detection parameters were set as follows: distance: 25 mm; a post-test speed: 5 mm/s; and force: 10 g.

2) The foam box and the petri dish were opened, and one cylindrical sample was quickly taken out and placed on the texture analyzer for calibration.

3) The detection data was exported, and the program was stopped. Texture analysis results of the four samples were 34213.56 g, 36589.92 g, 34793.36 g and 35277.08 g, respectively, which were averaged (35218.48 g) as the texture detection result of the back of the *Takifugu obscurus* sample.

EXAMPLE 2

Provided herein was a method for detecting a texture of *Takifugu obscurus*, in which a sample was cut from a head of *Takifugu obscurus* (as shown in the FIGURE). The method was specifically performed as follows.

1. Pre-treatment of *Takifugu obscurus* and Preparation of Containers

1) The abdomen of *Takifugu obscurus* was quickly cut open using a sharp scissor for bloodletting. The gill was cut and removed with internal organs using fingers, and then the remaining internal organ was trimmed with the scissor. The skin of *Takifugu obscurus* was peeled off along a cut line on an upper abdomen. Eyes of *Takifugu obscurus* were removed using the scissor. The blood remaining in a spine of *Takifugu obscurus* was squeezed out, and then the *Takifugu obscurus* was cleaned with ice water.

2) A clean disposable plastic wrap was laid on a test bench, and the *Takifugu obscurus* was placed on the plastic wrap and dried naturally for 40 min.

3) Crushed ice was loaded to a foam box to ½ by volume of the foam box, where the foam box had a size of 30 cm×20 cm×20 cm.

4) A disposable petri dish with a diameter of 9 cm was prepared, and cooled in a 4° C. refrigerator for 2 h to load the *Takifugu obscurus* sample.

2. Cutting of *Takifugu obscurus* Samples for Texture Analysis

1) A special sampling knife was cleaned, disinfected with 75% alcohol and dried.

2) The head of *Takifugu obscurus* was crosswise cut off along a junction between the head and the upper abdomen with the special sampling knife, and a flesh on each side of *Takifugu obscurus* was cut off completely along the spine. An upper end of the flesh was cylindrical and had a diameter of about 2.2 cm; a lower end of the flesh was flat and had a width of 2.5 cm; and the flesh had a length of about 14 cm.

3) A cylindrical sample with a height of about 2.0 cm and a diameter of about 2.2 cm was cut in parallel from a cross section of the cylindrical end, and quickly placed in a pre-cooled petri dish in a refrigeration box at 0-4° C. The cross section of the cylindrical sample clung to the petri dish. A petri dish cover was covered to fix the section of cylindrical sample, and then the refrigeration box was closed.

4) Another cylindrical sample was cut from the same *Takifugu obscurus* sample again in the same way, and was put into the pre-cooled petri dish in the foam box. Then two sections of cylindrical samples were cut from another flesh through the same operation method, and were quickly put into the pre-cooled petri dish in the foam box. As a consequence, a total of four cylindrical samples with nearly the same shape, diameter and height were collected and placed together in the pre-cooled petri dish.

3. Texture Analysis

The texture analyzer and program were started, and detection parameters were set as follows: distance: 25 mm; a post-test speed: 5 mm/s; and force: 10 g.

2) The foam box and the petri dish were opened, and one cylindrical sample was quickly taken out and placed on the texture analyzer for calibration.

3) The detection data was exported, and the program was stopped. Texture analysis results of the four samples were 19276.23 g, 26295.54 g, 16449.73 g and 24293.15 g, respectively, which were averaged (21578.66 g) as the texture detection result of the head of the *Takifugu obscurus* sample.

EXAMPLE 3

Provided herein was a method for detecting a texture of *Takifugu obscurus*, in which a sample was cut from a tail of *Takifugu obscurus* (as shown in the FIGURE). The method was specifically performed as follows.

1. Pre-treatment of *Takifugu obscurus* and Preparation of Containers

1) The abdomen of *Takifugu obscurus* was quickly cut open using a sharp scissor for bloodletting. The gill was cut and removed with internal organs using fingers, and then the remaining internal organ was trimmed with the scissor. The skin of *Takifugu obscurus* was peeled off along a cut line on an upper abdomen. Eyes of *Takifugu obscurus* were removed using the scissor. The blood remaining in a spine of *Takifugu obscurus* was squeezed out, and then the *Takifugu obscurus* was cleaned with ice water.

2) A clean disposable plastic wrap was laid on a test bench, and the *Takifugu obscurus* was placed on the plastic wrap and dried naturally for 40 min.

3) Crushed ice was loaded to a foam box to ½ by volume of the foam box, where the foam box had a size of 30 cm×20 cm×20 cm.

4) A disposable petri dish with a diameter of 9 cm was prepared, and cooled in a 4° C. refrigerator for 2 h to load the *Takifugu obscurus* sample.

2. Cutting of *Takifugu obscurus* Samples for Texture Analysis

1) A special sampling knife was cleaned, disinfected with 75% alcohol and dried.

2) The head of *Takifugu obscurus* was crosswise cut off along a junction between the head and the upper abdomen with the special sampling knife, and a flesh on each side of *Takifugu obscurus* was cut off completely along the spine. An upper end of the flesh was cylindrical and had a diameter of about 2.2 cm; a lower end of the flesh was flat and had a width of 2.5 cm; and the flesh had a length of about 14 cm.

3) A cylindrical sample with a height of about 2.0 cm and a diameter of about 2.2 cm was cut in parallel at a distance of 8.0 cm from a cross section of the cylindrical end, and quickly placed in a pre-cooled petri dish in the refrigeration box at 0-4° C. The cross section of the cylindrical sample clung to the petri dish. A petri dish cover was covered to fix the cylindrical sample, and then the refrigeration box was closed.

4) Another cylindrical sample was cut from the same *Takifugu obscurus* sample again in the same way, and was put into the pre-cooled petri dish in the foam box. Then two sections of cylindrical samples were cut from another flesh through the same operation method, and were quickly put into the pre-cooled petri dish in the foam box. As a consequence, a total of four cylindrical samples with nearly the same shape, diameter and height were collected and placed together in the pre-cooled petri dish.

3. Texture Analysis

1) The texture analyzer and program were started, and detection parameters were set as follows: distance: 25 mm; a post-test speed: 5 mm/s; and force: 10 g.

2) The foam box and the petri dish were opened, and one cylindrical sample was quickly taken out and placed on the texture analyzer for calibration.

3) The detection data was exported, and the program was stopped. Texture analysis results of the four samples were 19959.66 g, 18385.35 g, 17353.28 g and 14395.16 g, respectively, which were averaged (17523.36 g) as the texture detection result of the tail of the *Takifugu obscurus* sample.

According to the detection results of Examples 1-3, it can be seen that the texture data obtained from the samples cut from the head are significantly different; the texture data obtained from the samples cut from the tail are significantly lower, which cannot characterize an actual texture of *Takifugu obscurus*; the texture data obtained from the sample cut from the back is relatively high and a difference is small, which can effectively characterize the texture of *Takifugu obscurus*. Therefore, it is preferable to use an experimental method of Example 1 as a standard to detect the texture of *Takifugu obscurus*.

Described above are only preferred embodiments of the present disclosure and are not intended to limit the present disclosure. It should be understood that any modifications, replacements and improvements made by those skilled in the art without departing from the spirit and scope of the present disclosure should fall within the scope of the present disclosure defined by the appended claims.

What is claimed is:

1. A method for detecting a texture of *Takifugu obscurus*, comprising:
   (S1) removing internal organs and skin of a *Takifugu obscurus* followed by washing and drying; and
   removing a head of the *Takifugu obscurus* and cutting a flesh on two sides of the *Takifugu obscurus* along a spine of the *Takifugu obscurus*;
   (S2) cutting a plurality of cylindrical samples with the same shape and size along two sides of the flesh followed by transfer to a pre-cooled petri dish;
   allowing a cross section of each of the plurality of cylindrical samples to cling to the pre-cooled petri dish followed by fixing with a petri dish cover; and
   storing the petri dish in seal at 0-4° C.; and
   (S3) detecting, by a texture analyzer, a texture of each of the plurality of cylindrical samples; wherein detection parameters of the texture analyzer are set as follows: distance: 20-30 mm; post-test speed: 3-8 mm/s; and force: 8-12 g; and
   averaging detection results of the plurality of cylindrical samples as a detection result of the texture of *Takifugu obscurus* wherein the plurality of cylindrical samples are cut from a part of the flesh at a distance of 2.0 cm from a cross section of an upper end of the flesh.

2. The method of claim 1, wherein an upper end of the flesh is cylindrical and has a diameter of 2.0-2.5 cm; a lower end of the flesh is flat and has a width of 2.3-2.8 cm; and a length of the flesh is 13-15 cm.

3. The method of claim 1, wherein each of the plurality of cylindrical samples has a height of 1.5-2.0 cm and a diameter of 1.8-2.5 cm.

4. The method of claim 3, wherein a number of the plurality of cylindrical samples is greater than or equal to 2.

5. The method of claim 4, wherein the number of the plurality of cylindrical samples is 4.

6. The method of claim 1, wherein the petri dish is pre-cooled to 0-4° C.

7. The method of claim 1, wherein in step (S2), the petri dish containing the plurality of cylindrical samples is stored at 0-4° C. in a refrigeration device.

8. The method of claim 7, wherein after removed from the refrigeration device, the plurality of cylindrical samples are required to be transferred to the texture analyzer within 30 seconds.

\* \* \* \* \*